United States Patent
Yakabe et al.

(10) Patent No.: US 7,034,551 B2
(45) Date of Patent: *Apr. 25, 2006

(54) ELECTROSTATIC CAPACITANCE DETECTION CIRCUIT AND MICROPHONE DEVICE

(75) Inventors: Masami Yakabe, Tokyo (JP); Naoki Ikeuchi, Tokyo (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/488,764

(22) PCT Filed: Sep. 6, 2002

(86) PCT No.: PCT/JP02/09139

§ 371 (c)(1),
(2), (4) Date: Sep. 29, 2004

(87) PCT Pub. No.: WO03/023422

PCT Pub. Date: Mar. 20, 2003

(65) Prior Publication Data

US 2005/0040833 A1  Feb. 24, 2005

(30) Foreign Application Priority Data

Sep. 6, 2001 (JP) .............................. 2001-269992

(51) Int. Cl.
*G01R 27/26* (2006.01)
(52) U.S. Cl. ....................................... 324/686; 324/658
(58) Field of Classification Search ............. 73/514.32; 324/658, 661, 681, 686
See application file for complete search history.

(56) References Cited

U.S. PATENT DOCUMENTS 4,918,376 A * 4/1990 Poduje et al. ................ 324/663
6,145,384 A * 11/2000 Ikeda et al. .................... 73/780
6,373,264 B1 * 4/2002 Matsumoto et al. ........ 324/667

FOREIGN PATENT DOCUMENTS

DE 3007426 A1 9/1981
DE 3221800 A1 12/1983
EP 1219967 A1 7/2002

(Continued)

OTHER PUBLICATIONS

Supplementary European Search Report, EP 02798044, dated Dec. 14, 2005.

*Primary Examiner*—Walter Benson
(74) *Attorney, Agent, or Firm*—Finnegan, Henderson, Farabow, Garrett & Dunner, L.L.P.

(57) ABSTRACT

An electrostatic capacitance detection circuit 10 comprises an AC voltage generator 11, a first operational amplifier 14 of which non-inverting input terminal is connected to specific potential (a ground in this example), a second operational amplifier 16 that includes a voltage follower, a resistance (R1) 12 connected between the AC voltage generator 11 and an inverting input terminal of the first operational amplifier 14, a resistance (R2) 13 connected between the inverting input terminal of the first operational amplifier 14 and an output terminal of the second operational amplifier 16, and an impedance element (a capacitor) 15 connected between an output terminal of the first operational amplifier 14 and a non-inverting input terminal of the second operational amplifier 16, and a capacitor to be detected 17 is connected between the non-inverting input terminal of the second operational amplifier 16 and specific potential. The electrostatic capacitance detection circuit 10 and the capacitor 17 are located adjacently.

9 Claims, 6 Drawing Sheets

FOREIGN PATENT DOCUMENTS

| | | |
|---|---|---|
| JP | 09-280806 | 10/1997 |
| JP | 2001-324520 | 11/2001 |
| JP | 2002-022785 | 1/2002 |
| JP | 2002-022786 | 1/2002 |
| JP | 2002-157671 | 5/2002 |
| WO | WO 99/38019 | 7/1999 |

\* cited by examiner

ELECTROSTATIC CAPACITANCE DETECTION CIRCUIT AND MICROPHONE DEVICE

TECHNICAL FIELD

The present invention relates to a circuit and a device that detect electrostatic capacitance, especially relates to the circuit, the device and a microphone device that detect very small capacitance with high accuracy.

BACKGROUND ART

Figure 1:
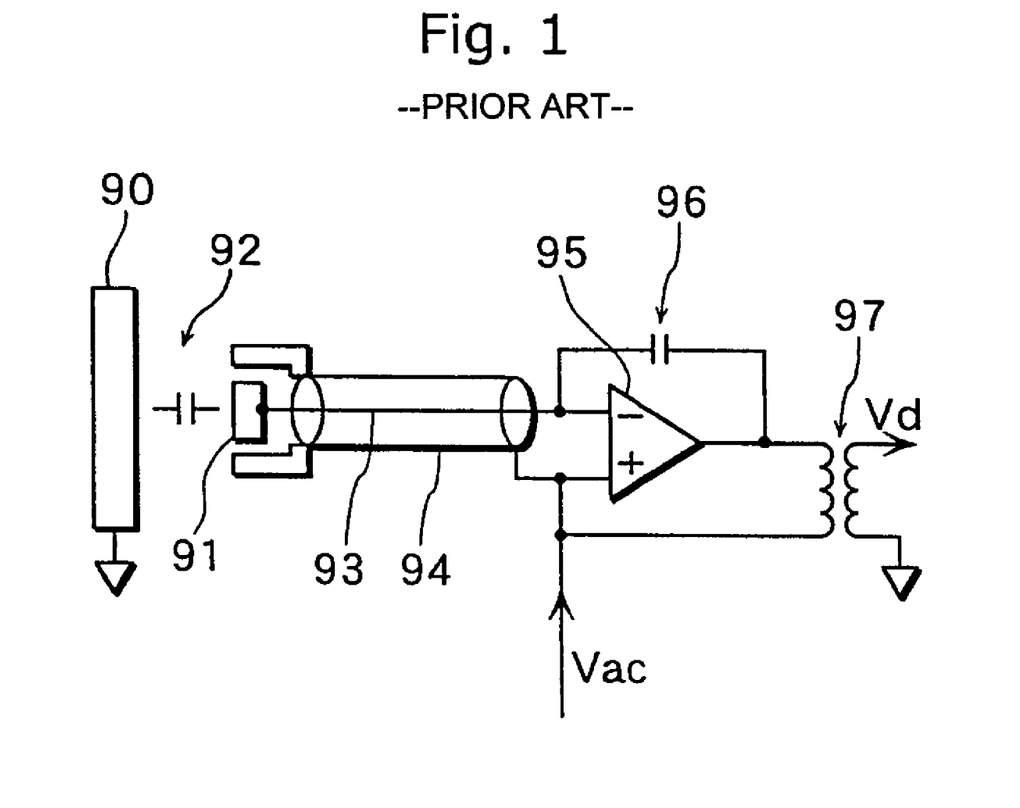
FIG. 1 is a circuit diagram showing a conventional electrostatic capacitance detection circuit.

As a prior art of an electrostatic capacitance detection circuit, that described in Japanese Laid-Open Patent Application H09-280806 gazette can be cited. FIG. 1 is a circuit diagram that shows this electrostatic capacitance detection circuit. In this detection circuit, a capacitive sensor 92 comprised of electrodes 90 and 91 is connected to an inverting input terminal of an operational amplifier 95 via a signal line 93. And a capacitor 96 is connected between an output terminal of this operational amplifier 95 and the said inverting input terminal, and further an AC voltage Vac is applied to a non-inverting input terminal. Also, the said signal line 93 is wrapped up by a shield line 94 and shielded electrically against disturbance noise. And this shield line 94 is connected to the non-inverting input terminal of the operational amplifier 95. Output voltage Vd is obtained from an output terminal of the said operational amplifier 95 via a transformer 97.

In this detection circuit, the inverting input terminal and the non-inverting input terminal of the operational amplifier 95 are in an imaginary short status, so that the signal line 93 connected to the inverting input terminal and the shied line 94 connected to the non-inverting input terminal have the almost same potential. Thereby, the signal line 93 is guarded by the shield line 94, that is, stray capacitance between the signal line 93 and the shield line 94 is canceled, and the output voltage Vd, which is unlikely to be affected by the stray capacitance, can be obtained.

According to this kind of conventional art, when capacitance of the capacitive sensor 92 is big to some extend, it is indeed possible to obtain accurate output voltage Vd, which is not affected by the stray capacitance between the signal line 93 and the shield line 94. However, when very small capacitance, which equals to or is less than an order of several pF or fF (femtofarad), is detected, an error is increased.

Also, depending on a frequency of the AC voltage Vac applied, a subtle displacement of a phase and amplitude consequently arises between the voltage of the inverting input terminal and that of the non-inverting input terminal, which are in the imaginary short status, due to a tracking error in the operational amplifier 59, and thereby the detection error becomes bigger.

On the other hand, for lightweight and small audio communication devices represented by a mobile phone or the like, there has been a demand of a compact amplifier circuit that sensitively and faithfully transforms sounds detected by a capacitive sensor such as a capacitor microphone into an electric signal. If it is possible to accurately detect very small capacitance that equals to or is less than several pF or fF and/or its change, a high performance microphone that can detect sounds with a very high level of sensitivity and fidelity is realized, and thereby performance for picking up sounds by the audio communication devices such as a mobile phone will make rapid progress.

This invention is devised in view of the above-mentioned situation, and aims at providing an electrostatic capacitance detection circuit and the like that are capable of accurately detecting very small capacitance, and suitable to detect capacitance of a capacitive sensor such as a capacitor microphone used for lightweight and compact audio communication devices.

DISCLOSURE OF INVENTION

In order to achieve above objectives, the electrostatic capacitance detection circuit according to the present invention is an electrostatic capacitance detection circuit that outputs a detection signal corresponding to electrostatic capacitance of a capacitor to be detected, comprising: a voltage follower of which input impedance is high and voltage gain is almost one; a first capacitive impedance element; an operational amplifier; an AC voltage generator that applies AC voltage to the operational amplifier; and a signal output terminal that is connected to an output of the operational amplifier, wherein an input terminal of the voltage follower is connected to one end of the capacitor and one end of the first impedance element, the first impedance element and the voltage follower are included in a negative feedback loop of the operational amplifier, and the capacitor and the electrostatic capacitance detection circuit are located adjacently.

Also, the electrostatic capacitance detection circuit according to the present invention is An electrostatic capacitance detection circuit that outputs a detection signal corresponding to electrostatic capacitance of a capacitor to be detected, comprising: a voltage follower of which input impedance is high and voltage gain is almost one; a first capacitive impedance element; an operational amplifier; an AC voltage generator that applies AC voltage to the operational amplifier; and a signal output terminal that is connected to an output of the operational amplifier, wherein an input terminal of the voltage follower is connected to one end of the capacitor and one end of the first impedance element, the first impedance element and the voltage follower are included in a negative feedback loop of the operational amplifier, and the capacitor, the first impedance element and the voltage follower are located closely.

As a specific example, the electrostatic capacitance detection circuit is structured to comprise an AC voltage generator, a first operational amplifier of which non-inverting input terminal is connected to specific potential, a second operational amplifier structuring a voltage follower, a resistance connected between an inverting input terminal of the first operational amplifier and an output terminal of the second operational amplifier, a capacitor (a first impedance element) connected between the output terminal of the first operational amplifier and the non-inverting input terminal of the second operational amplifier. A capacitor to be detected is connected between the non-inverting input terminal of the second operational amplifier and the specific potential, and the electrostatic capacitance detection circuit and the capacitor to be detected are located adjacently or are set closely at a short distance that does not make the stray capacitance of the signal line exceed ten times as much as maximum capacitance of an element connected. The specific potential in the example here indicates either certain standard potential, specific DC potential, ground potential or a floating status, whichever suitable is selected according to a style of an embodiment. Also, a second impedance element (resistance) connected between the AC voltage generator and the inverting input terminal of the first operational amplifier may further be added.

According to the above structure, a certain voltage is applied to the capacitor to be detected, most of electric current that flows through the capacitor to be detected is further sent to the capacitor (the first impedance element), and then a signal corresponding to the electrostatic capacitance of the capacitor to be detected is output from a signal output terminal.

Here, the capacitor to be detected and the electrostatic capacitance detection circuit are located as adjacently as possible to reduce noise mixed in the signal line, which connects the electrostatic capacitance detection circuit with the capacitor to be detected, and also reduce the stray capacitance generated at the signal line. Or, the capacitor to be detected, the first impedance element and the voltage follower are located as closely as possible.

In this patent document, "closely" means that the stray capacitance of the signal line is in a situation where the capacitance does not exceed ten times as much as a bigger value of either the capacitance value of the capacitor to be detected or the capacitance value of the first capacitive impedance element. It was found through experiences that the electrostatic capacitance detection circuit of the present invention can prevent its detection sensitivity from being highly deteriorated when the stray capacitance of the signal line is set to have a capacitance value that does not exceed ten times as much as the capacitance value of the element connected. This stray capacitance of the signal line is measurable if it is measured under a situation where the capacitor to be detected, the first impedance element and the voltage follower are not connected to the signal line. In this patent document, a status where an object is in contact with other object side by side under the above condition for being closely is called as "adjacently".

Also, in addition to the said electrostatic capacitance detection circuit, it is possible to add an inverting amplify circuit that inverts the signal at the signal output terminal and an adding circuit that adds up an output signal of the voltage follower and an output signal of the inverting amplify circuit. Also, resistance may be connected in parallel with the capacitor (the first impedance element).

As a practical application of the present invention, it is preferable that the capacitor to be detected is a capacitance type of sensor that detects a physical quantity according to a fluctuation in the capacitance, that the electrostatic capacitance detection circuit is formed on a printed circuit board or a silicon substrate, and that the capacitance type of sensor and the board are fixed or composed as one. As a further specific example, it is more preferable that a capacitor microphone is adopted as the capacitor to be detected, that the electrostatic capacitance detection circuit is embodied by an IC, that the capacitor microphone and the IC are integrated into one and put in a shield box as a microphone used for a mobile phone or the like. In this case, the capacitor microphone and the IC are fixed adjacently and connected with a conductive board, a wiring pattern, a wire bonding or the like.

BEST MODE FOR CARRYING OUT THE INVENTION

The following provides a detailed explanation of embodiments of the present invention with reference to diagrams.

(First Embodiment)

Figure 2:
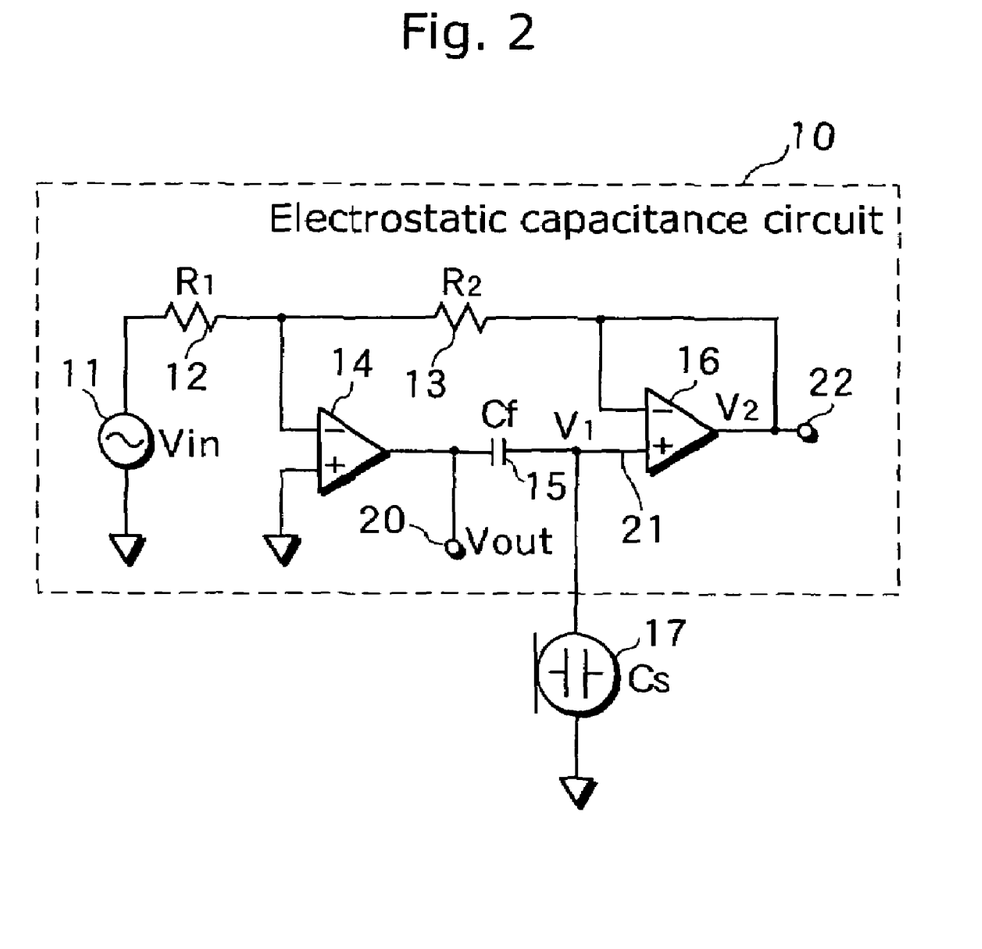
FIG. 2 is a circuit diagram of an electrostatic capacitance detection circuit according to a first embodiment of the present invention.

FIG. 2 is a circuit diagram of an electrostatic capacitance detection circuit 10 according to a first embodiment of the present invention. In this diagram, this electrostatic capacitance detection circuit 10 is connected to a capacitor to be detected 17 that is a subject for detection (i.e. a capacitance type sensor that detects various types of physical quantities using a fluctuation in the electrostatic capacitance Cs such as a capacitor microphone in this example.)

This electrostatic capacitance detection circuit 10 comprises an AC voltage generator 11 that generates AC voltage, a resistance (R1) 12, a resistance (R2) 13, a first operational amplifier 14, an impedance element 15 (a capacitor with capacitance Cf in this example) and a second operational amplifier 16, and outputs a detection signal (voltage V out) corresponding to electrostatic capacitance of the capacitor 17 from a signal output terminal 20.

One end of the AC voltage generator 11 is connected to specific electrical potential (a ground in this example), and other end (an output terminal) of that generates specific AC voltage (voltage V in, angular frequency $\omega$). The resistance (R1) 12 is connected between the output terminal of the AC voltage generator 11 and an inverting input terminal of the first operational amplifier 14.

The first operational amplifier 14 is a voltage amplifier with a high level of input impedance and an open loop gain, a non-inverting input terminal here is connected to specific potential (the ground in this example), and the non-inverting input terminal and the inverting input terminal are in an imaginary short status. In a negative feedback loop of the first operational amplifier 14, which is from an output terminal to the inverting input terminal of the first operational amplifier 14, the capacitor 15, the second operational amplifier 16 and the resistance (R2) 13 are connected in series in this order.

The second operational amplifier 16, of which inverting input terminal is connected to an output terminal, includes a voltage follower of which input impedance is extremely high, output impedance is extremely low, and voltage gain is almost 1. A non-inverting input terminal 21 of this second operational amplifier 16 is connected to one end of the capacitor 17 via a signal line or an electric conductor such as a wiring pattern on a printed circuit board, and other end of the capacitor 17 is connected to specific potential (the ground in this example). An output terminal of the first operational amplifier 14 is connected to an output signal of this electrostatic capacitance detection circuit 10, i.e. the signal output terminal 20 for outputting a detection signal corresponding to the capacitance of the capacitor 17.

As for the connection between the capacitor 17 and the electrostatic capacitance detection circuit 10, it is preferable that an electric conductor, which is as short as possible, (such as a cable, a copper foil wiring pattern, a connection terminal) is used, so that it is possible to prevent any unnecessary stray capacitance from being added as a detection error, or a disturbance noise from being mixed. Moreover, to enhance a shield against the disturbance noise, it is preferable that a whole part of the capacitor 17 and the electrostatic capacitance detection circuit 10 is covered with a grounded shield material or put in a shield box if possible.

Actions of the electrostatic capacitance detection circuit 10 structured above are as follows.

Regarding an inverting amplification circuit comprising the resistance (R1) 12, the resistance (R2) 13 and the first operational amplifier 14 and the like, both of the input terminals of the first operational amplifier 14 are in the imaginary short status and in the same potential (e.g. 0 V), their impedance is extremely high, and no electric current flows through, so that the electric current passed through the resistance (R1) 12 becomes Vin/R1. Because all of the electric current is passed through the resistance (R2) 13, the following expression becomes effective when the output voltage of the second operational amplifier 16 is V2.

$$V\text{in}/R1 = -V2/R2$$

When summarizing this, the output voltage V2 of the second operational amplifier 16 can be expressed by the following expression.

$$V2 = -(R2/R1) \cdot V\text{in} \quad \text{(Expression 1)}$$

Also, because the second operational amplifier 16 includes the voltage follower, both of the input terminals are in the imaginary short status, and the input voltage V1 (voltage of the non-inverting input terminal 21) equals to the output voltage V2 (voltage of the inverting input terminal and the output terminal 22), so that the input voltage V1 is expressed as follows.

$$V1 = V2 \quad \text{(Expression 2)}$$

That is, because the first operational amplifier 14 is to get a gain sufficiently, actions thereof are more stabilized by connecting the non-inverting input to specific potential. Also, since the gain of the second operational amplifier 16 is 1, and the voltages of the inverting input and output are determined, the voltage of the non-inverting input is accordingly decided. In the way like this, as the amplifier to obtain the gain sufficiently is separated from the amplifier to decide the voltage, it is possible to improve their respective stability and widely reduce operational errors.

When the electric current that flows from the capacitor 15 towards the capacitor 17 is i, all of the electric current i is sent to the capacitor 17 because the input impedance of the second operational amplifier 16 is extremely high. Therefore, the electric current i becomes jωC·V1. The voltage Vout of the detection signal output from the signal output terminal 20 is expressed as follows:

$$V\text{out} = i \cdot (1/j\omega Cf) + V1 \quad \text{(Expression 3)}$$
$$= (1 + Cs/Cf) \cdot V1$$

When V2 is deleted from the above expressions 1 and 2, the following expression is obtained.

$$V1 = -(R2/R1) \cdot V\text{in} \quad \text{(Expression 4)}$$

When this V1 is assigned to the above expression 3, the following expression is obtained.

$$V\text{out} = -(1 + Cs/Cf) \cdot (R2/R1) \cdot V\text{in} \quad \text{(Expression 5)}$$

As clarified from this expression 5, the voltage Vout of the detection signal output from the signal output terminal 20 of the electrostatic capacitance detection circuit 10 becomes a value that depends on the capacitance Cs of the capacitor 17. Therefore, the capacitance Cs can be determined by executing various signal processing to this voltage Vout. Also, as seen in this expression 5 where the angular frequency ω is not included, the voltage Vout of this detection signal does not depend on a fluctuation in a frequency of the AC signal Vin from the AC voltage generator 11 and in a frequency of the capacitor 17. So, the electrostatic capacitance detection circuit (that does not have a frequency-dependent characteristic in the circuit) capable of detecting the capacitance of the capacitor 17 is realized without depending on the frequency of the AC voltage applied to the capacitor 17. Therefore, for the capacitor 17, of which capacitance value is changed at a certain frequency (sound band), such as a capacitor microphone, it is possible to specify a capacitance value directly from the voltage value thereof in stead of correcting the frequency for the detected signal.

Also, in the electrostatic capacitance detection circuit 10 according to this embodiment, the first operational amplifier 14, which supplies the electric current to the capacitor 15 and the capacitor 17, has the non-inverting input terminal connected to specific potential and fixed. Therefore, unlike the operational amplifier 95 in the conventional circuit shown in FIG. 1, the first operational amplifier 14 supplies stable electric current with less noises to the capacitor 15 and the capacitor 17 without depending on the frequency of the input AC signal or the like, and very small capacitance of the capacitor 17 can be detected.

According to an experiment related to the present invention, in the electrostatic capacitance detection circuit shown in FIG. 2, for example, if the stray capacitance of the signal line exceeds 200 pF when original electrostatic capacitance of Cs (a capacitor to be detected: a microphone in the present embodiment) is 20 pF, the detection sensitivity becomes much worse. Also, when the said Cs is checked with a few other electrostatic capacitance values, their results tend to be the same.

Additionally, both of the capacitance Cf, which is the first impedance element, and the capacitor Cs are a capacitance element connected to the signal line in this circuit, so that the same result as above is expected for calculation of both of the elements.

From these experimental results and experiences, it was found out that good detective sensitivity is secured when the capacitor to be detected, the first impedance element and the voltage follower are located closely in a way that the stray capacitance of the signal line does not exceed ten times as much as the capacitance value of the relevant Cs or Cf.

(Second Embodiment)

Next, the following describes an electrostatic capacitance detection circuit according to a second embodiment of the present invention.

Figure 3:
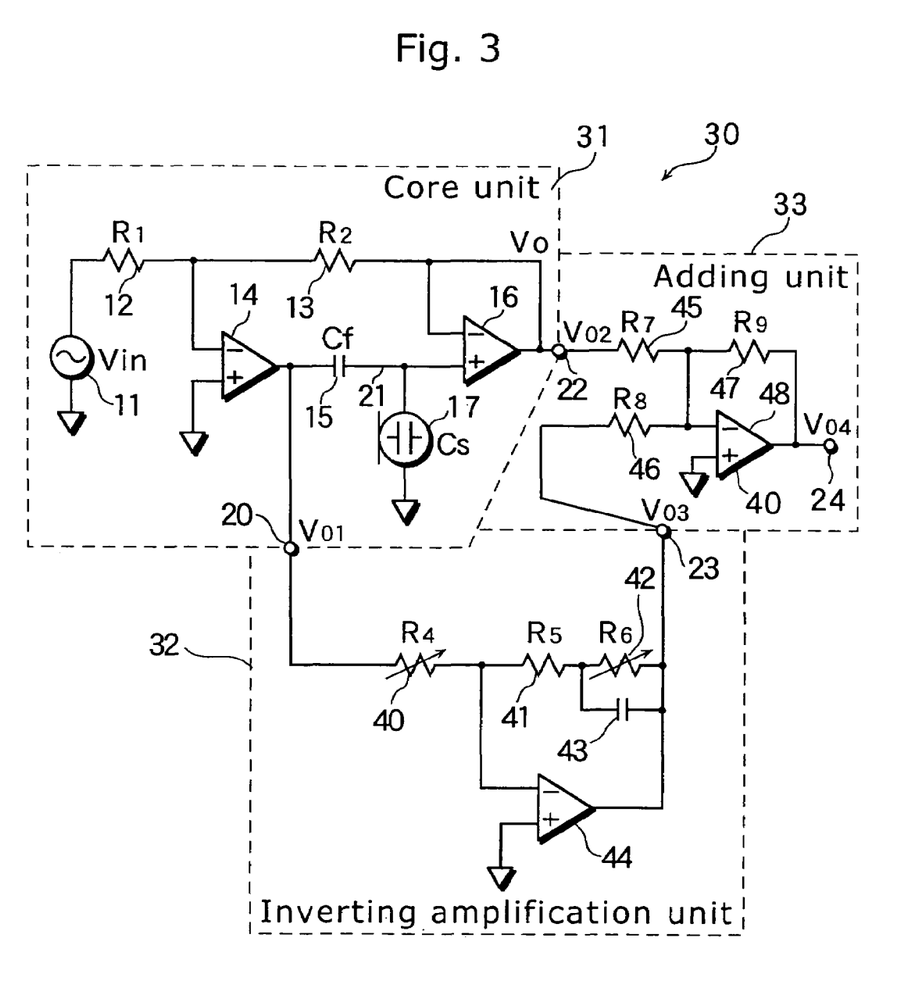
FIG. 3 is a circuit diagram of an electrostatic capacitance detection circuit according to a second embodiment of the present invention.

FIG. 3 is a circuit diagram of an electrostatic capacitance detection circuit 30 in the second embodiment. This electrostatic capacitance detection circuit 30 is roughly composed of a core unit 31 equivalent to the electrostatic capacitance detection circuit 10 shown in FIG. 2, an inverting unit 32 that receives signal voltage V01 at a signal output terminal 20 of the core unit 31 as an input and inverts the signal voltage V01, an adding unit 33 that adds up signal voltage V03 at an output terminal 23 of the inverting unit 32 and signal voltage V02 at an AC output terminal 22 of the core unit 31 and outputs a detection signal of voltage V04 to an output terminal 24.

The core unit 31 has the same circuit as the electrostatic capacitance detection circuit 10 shown in FIG. 2. Therefore, according to the above expression 5, the voltage V01 of the signal output terminal 20 of the core unit 31 is as follows:

$$V01 = -(1+Cs/Cf) \cdot (R2/R1) \cdot Vin \quad \text{(Expression 6)}$$

According to the above expression 1, the voltage V02 of the AC output terminal 22 of the core unit 31 is as follows:

$$V02 = -(R2/R1) \cdot Vin \quad \text{(Expression 7)}$$

The inverting unit 32 is an inverting amplification circuit comprising a variable resistance (R4) 40, a resistance (R5) 41, a variable resistance (R6) 42, a capacitor 43 and an operational amplifier 44, of which voltage gain is −1, and resistance values of the variable resistance (R4) 40 and the variable resistance (R6) 42 are adjusted to have a phase of the signal V03 at the output terminal 23 identical to the one of the signal V02 at the AC output terminal 22 of the core unit 31. Therefore, the following relation is ideally established between the input voltage V01 and the output voltage V03 of this inverting unit 32.

$$V03 = -V01 \quad \text{(Expression 8)}$$

The adding unit 33 is an adding device of which three resistances (R7) 45, (R8) 46 and (R9) 47 having the same resistance value are connected to an operational amplifier 48. So, the following relation is established among two input signals of the voltage V02 and the voltage V03 and the output voltage V04.

$$V04 = -(V02+V03) \quad \text{(Expression 9)}$$

After the above expression 8 is assigned to this expression 9 and V03 is deleted, the above expressions 6 and 7 are assigned to it. Then, the following expression becomes effective.

$$V04 = V01 - V02 \quad \text{(Expression 10)}$$
$$= -(Cs/Cf) \cdot (R2/R1) \cdot Vin$$

Accordingly, the voltage V04 of the detection signal output from the output terminal 24 of this electrostatic capacitance detection circuit 30 is in proportion to the capacitance value Cs. Therefore, unknown capacitance value Cs and a fluctuation in the capacitance can be easily specified by executing various signal processing based on this voltage V04.

As clarified from comparison between this expression 10 and the expression 5 that indicates the voltage Vout of the detection signal according to the first embodiment, unlike the first embodiment 30, the detection signal obtained by the electrostatic capacitance detection circuit 30 according to the second embodiment contains only a component being in proportion to the capacitance of the capacitor 17, and does not contain any unnecessary offset (i.e. the voltage that does not depend on the capacitor 17). Therefore, signal processing according to the second embodiment, which specifies capacitance or a fluctuation in the capacitance of the capacitor 17 from the detection signal, can be simple.

Although a case of V03=−V01 is used in this example, the present invention is not limited to this. According to a type of the capacitive sensor, the output voltage V04 can be set as follows with a case of V03=k·V01 (k is an amplification ratio of an inverting amplification unit).

$$V04 = \{k \cdot (Cs/Cf) + (k+1)\} \cdot (R2/R1) \cdot Vin$$

Figure 4:
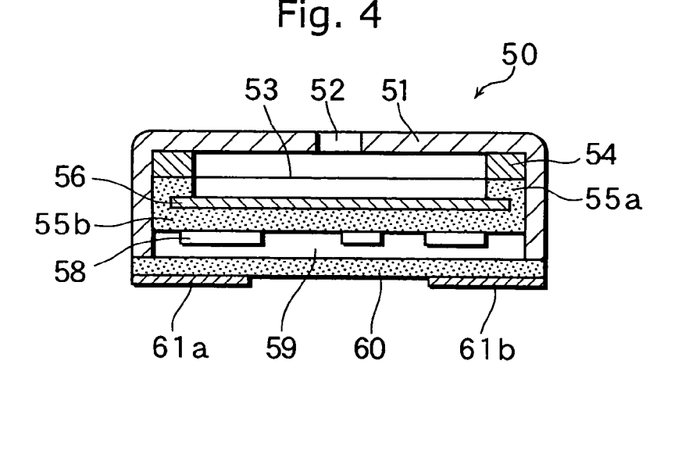
FIG. 4 is a diagram showing a practical example of the electrostatic capacitance detection circuit of the present invention used for electric devices (a cross section diagram of a microphone).

FIG. 4 is a diagram showing a practical example to use the electrostatic capacitance detection circuit according to the first and second embodiments for an electric device. Here, it shows a cross section diagram of a microphone 50 used for a mobile phone or the like which comprises a capacitor microphone and an electrostatic capacitance detection circuit that are integrated into one. This microphone 50 comprises a lid cover 51 having a sound hole 52, an oscillating film 53 that oscillates with sounds, a ring 54 that fixes the oscillating film 53, a spacer 55a, a fixed electrode 56 set up against the oscillating film 53 via the spacer 55a, an isolation board 55b that supports the fixed electrode 56, an IC chip 58 forming the electrostatic capacitance detection circuit according to the above embodiment, which is fixed on a backside of the isolation board 55b, an IC package 59 that molds the IC chip 58, external electrodes 61a and 61b that are connected by the IC chip 58, a wire bonding, a contact hole, or the like.

The oscillating film 53, which is one side of the electrodes that forms the capacitor, is connected to specific potential (a ground in this example), and the fixed electrode 56, which is the other side of the electrodes, is connected to a circuit of the IC chip 58 via an electric conductor such as an aluminum board, a wire bonding, or a contact hole. Capacitance and a change in the capacitance of the capacitor comprising the oscillating film 53 and the fixed electrode 56 are detected by the electrostatic capacitance detection circuit in the IC chip 58 located adjacently via the isolation board 55b, transformed into an electric signal, and output from the external electrodes 61a and 61b, or the like. The lid cover 51, which is made from a metal such as aluminum, serves as a role of a shield box that shields any disturbance noise mixed into the inner capacitors 53 and 56, and the IC chip 58 with a conductive film (not shown) formed on an upper surface of the isolation board 60. In this example, the fixed electrode 56 is connected to the circuit, and the oscillating film 53 is connected to specific potential. However, the oscillating film 53 may be connected to the circuit, and the fixed electrode 56 may be connected to the specific potential. But, the former case is preferable from past experiences.

Figure 5A:
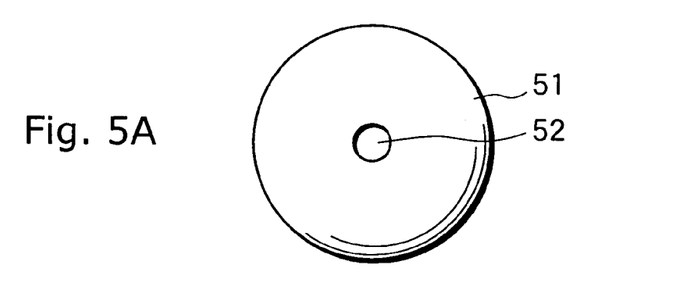
FIG. 5A is a plain diagram showing an external outline of the microphone shown in FIG. 4.
Figure 5B:
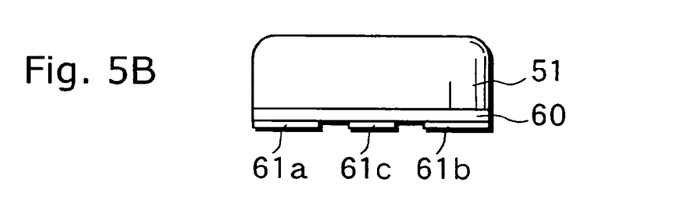
FIG. 5B is a front view diagram showing the external outline of the microphone shown in FIG. 4.
Figure 5C:
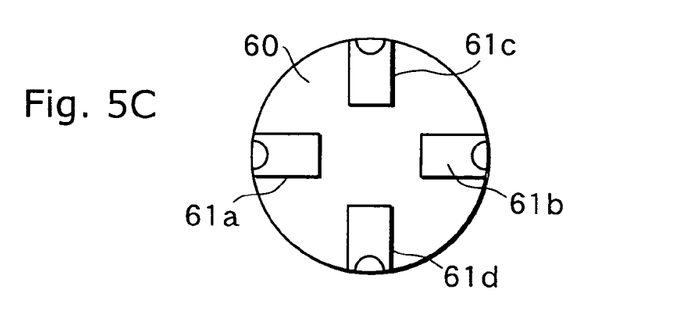
FIG. 5C is a bottom view diagram showing the external outline of the microphone shown in FIG. 4.

FIG. 5 is an external view diagram showing an outline of the microphone 50 shown in FIG. 4. FIG. 5A is a plain diagram, FIG. 5B is a front view, and FIG. 5C is a bottom view diagram showing the external outline of the microphone shown in FIG. 4. Size of the lid cover 51 shown in FIG. 5A and FIG. 5B is, for example, approximately φ5 mm×2 mm in height. Four external electrodes 61a~61d shown in FIG. 5C are, for example, two terminals for a power supply and two terminals for an output signal of the electrostatic capacitance detection circuit.

In such a practical example, the capacitor to be detected (the capacitor microphone in the example here) and the electrostatic capacitance detection circuit (the IC chip in the example here) are located adjacently, the signal line is extremely short, and the stray capacitance thereof is connected by an electric conductor of which length does not exceed ten times as much as a bigger capacitance value of either the capacitor microphone or the first impedance element in the circuit. Then, these parts are covered with a shield material such as a metal lid cover. Therefore, in the practical example like this, any negative impacts such as disturbance noise, which is mixed into the signal line(the electric conductor) connecting the capacitor to be detected and the electrostatic capacitance detection circuit, can be ignored.

Figure 6:
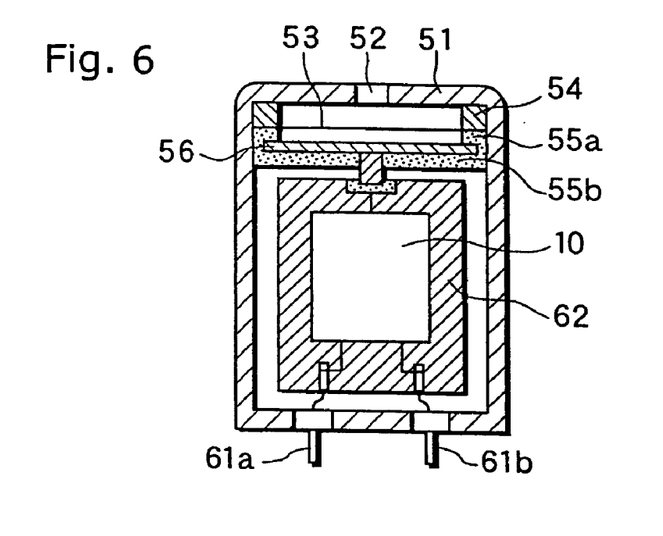
FIG. 6 is a cross section diagram of other example of the microphone.
Figure 7A:
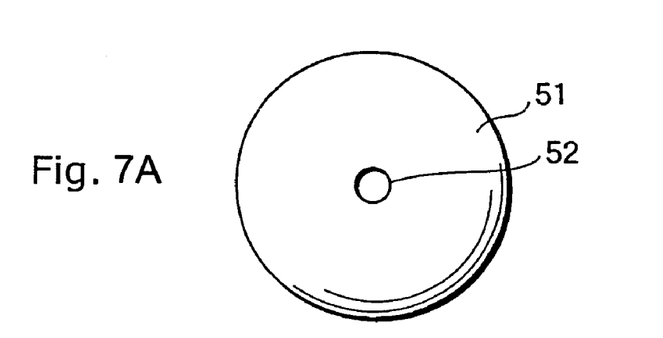
FIG. 7A is a plain diagram showing an external outline of the microphone shown in FIG. 6.
Figure 7B:
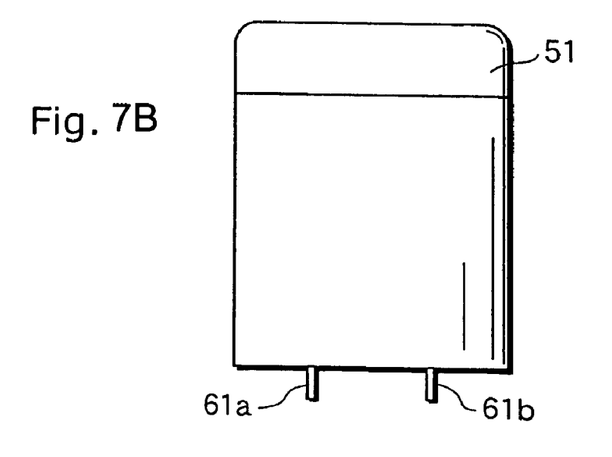
FIG. 7B is a front view showing the external outline of the microphone shown in FIG. 6.

That is, in a compact microphone like this, since the capacitor to be detected and the electrostatic capacitance detection circuit are connected each other by an extremely short electric conductor, connecting them by a shield cable and using a special circuit for applying guard voltage to the shield make the size of the circuit rather bigger and impede miniaturization of the circuit. Therefore, it is preferable that the capacitor to be detected and the electrostatic capacitance detection circuit are connected by a non-shielded (unshielded) conductive board, wiring pattern, wire bonding, lead line or the like through a shortest route. As other example of the microphone, FIG. 6 and FIG. 7 show the circuit put on a board. It is basically the same as the one in FIG. 4 with the exception of the electrostatic capacitance detection circuit put on a board 62.

Although the electrostatic capacitance detection circuit according to the present invention has been described based on the two embodiments and the practical examples applied to a product, the present invention is not limited to these embodiments and practical examples.

For instance, in the electrostatic capacitance detection circuits 10 and 30, the capacitor 15 is connected between the first operational amplifier 14 and the second operational amplifier 16 to detect electric current passed through the capacitor 17, but an impedance element such as a resistance or an inductance may be connected.

Figure 8:
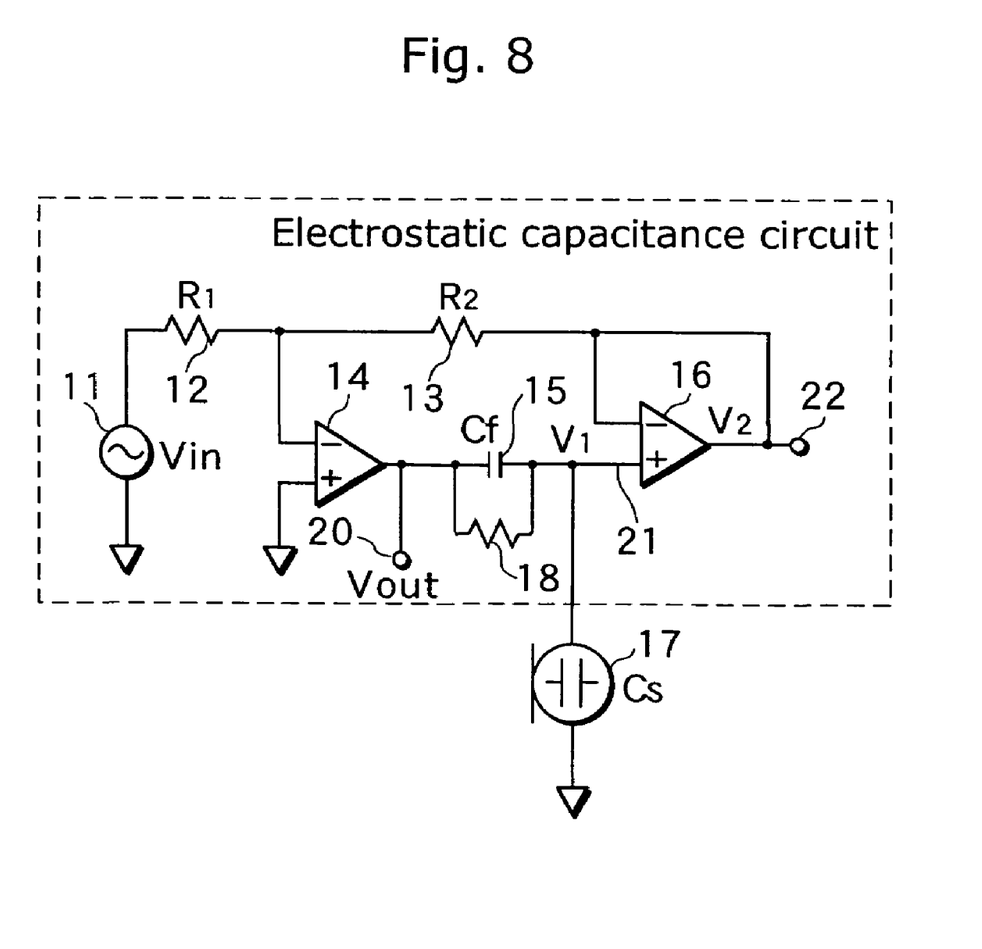
FIG. 8 is a circuit diagram of the electrostatic capacitance detection circuit according to other embodiment of the present invention.

Also, as shown in FIG. 8, it is possible to connect a resistance 18 in parallel with the capacitor 15 in the electrostatic capacitance detection circuits 10 and 30 according to the above embodiments. In this way, a connecting point for the capacitor 15 and the capacitor 17 is connected to the output terminal of the first operational amplifier 14 via the resistance 18, so that having a floating status through a DC form can be avoided and the potential can be fixed.

Also, a capacitive sensor connected as the capacitor 17 is not limited to a capacitor microphone and includes all of transducers (devices), which detect various physical quantities using a change in the electrostatic capacitance, such as an acceleration sensor, a seismograph, a pressure sensor, a displacement sensor, a proximity sensor, a touch sensor, an ion sensor, a humidity sensor, a raindrop sensor, a snow sensor, a thunder sensor, a placement sensor, a bad contact sensor, a configuration sensor, an endpoint detection sensor, an oscillation sensor, an ultrasonic wave sensor, an angular velocity sensor, a liquid quantity sensor, a gas sensor, an infrared rays sensor, a radiation sensor, a water gauge, a freeze sensor, a moisture meter, a vibrometer, an electrification sensor, a publicly-known capacitive type sensor like a printed circuit board inspection device, or the like.

As has been clarified from the above explanation, by applying AC voltage to the operational amplifier via the resistance and connecting the capacitance to be detected to the signal line, the electrostatic capacitance detection circuit, the electrostatic capacitance detection device and the microphone device according to the present invention detect capacitance of the capacitor to be detected. That is, the capacitor is connected between the output terminal of the operational amplifier, of which non-inverting input terminal is connected to the specific potential, and the input terminal of the voltage follower, and further the capacitor to be detected is connected between the input terminal of the voltage follower and the specific potential.

In this way, all of electric current sent to the capacitor to be detected flows to the capacitor, so that an accurate signal corresponding to the capacitance of the capacitor to be detected is output to the output terminal of the operational amplifier, which makes it possible to detect very small capacitance that equals to or is less than several pF or fF.

Then, because the non-inverting input terminal of the operational amplifier is connected to the specific potential, and the potential at one end of the input terminal is fixed, the operational amplifier is functioned steadily, the operational error is reduced, and the noise mixed in the detection signal is restrained.

Also, since the capacitor is connected between the operational amplifier and the voltage follower, detection sensitivity, which does not depend on a frequency of the AC voltage applied to the operational amplifier and on a frequency of a change in the capacitance of the capacitor to be detected, is secured. Moreover, when the resistance is connected between the operational amplifier and the voltage follower, it does not cause a problem to degrade an S/N ratio due to thermal noise from the resistance.

By placing this electrostatic capacitance detection circuit adjacent to the capacitor to be detected, or placing a circuit element connected to the signal line closely, a shield cable connecting between them and a special circuit that cancels stray capacitance generated by the cable become unnecessary.

Here, it is possible to add the inverting amplification circuit that inverts a signal at the signal output terminal and the adding circuit that adds up the output signal of the voltage follower and the output signal of the inverting amplification circuit to the said electrostatic capacitance detection circuit. By doing so, any unnecessary offset component contained in the output signal of the electrostatic capacitance detection circuit is removed, and a net signal corresponding to the capacitance of the capacitor to be detected can be amplified significantly.

Also, the capacitor to be detected may be embodied as a capacitor microphone, the electrostatic capacitance detection circuit may be embodied as an IC, and the capacitor microphone and the IC may be integrated into one and put in a shield box as a microphone used for a mobile phone or the like, so that the capacitor microphone and the electrostatic capacitance detection circuit are located very adjacently, and it becomes unnecessary to have a shield cable with a big diameter, which connects the capacitor to be detected and the electrostatic capacitance detection circuit, and a special circuit for applying guard voltage, or the like.

Additionally, as the electrostatic capacitance detection circuit according to the present invention detects capacitance by sending electric current to the capacitor to be detected, it does not need to paste a highly polymerized film or the like to the electrode of the capacitor to be detected and have it electret like an electret capacitor microphone so that it is applicable to a normal electrostatic capacitance type sensor.

As has been mentioned, the present invention reduces limitation for a usage environment, detects very small capacitance accurately, and realizes an electrostatic capacitance detection circuit or the like that is suitable for miniaturization, and especially sound performance of lightweight and compact audio communication devices such as a mobile phone is rapidly improved and its practical value is extremely high.

Industrial Applicability

The electrostatic capacitance detection circuit according to the present invention may be used as a detection circuit of a capacitance type sensor, especially as a microphone device that is equipped with compact and lightweight devices such as a mobile phone.

What is claimed is:

1. An electrostatic capacitance detection circuit that outputs a detection signal corresponding to electrostatic capacitance of a capacitor to be detected, comprising:
    a voltage follower of which input impedance is high and voltage gain is almost one;
    a first capacitive impedance element;
    an operational amplifier;
    an AC voltage generator that applies AC voltage to the operational amplifier; and
    a signal output terminal that is connected to an output of the operational amplifier,
    wherein an input terminal of the voltage follower is connected to one end of the capacitor and one end of the first capacitive impedance element,
    the first capacitive impedance element and the voltage follower are included in a negative feedback loop of the operational amplifier, and
    the capacitor and the electrostatic capacitance detection circuit are located adjacently.

2. The electrostatic capacitance detection circuit according to claim 1,
    wherein the capacitor, the first capacitive impedance element, and the voltage follower are located closely.

3. The electrostatic capacitance detection circuit according to claim 1,
    wherein the electrostatic capacitance detection circuit further includes a resistance element connected in parallel with the first capacitive impedance element.

4. The electrostatic capacitance detection circuit according to claim 1,
    wherein a second impedance element is further included between the AC voltage generator and the operational amplifier.

5. The electrostatic capacitance detection circuit according to claim 1,
    wherein the electrostatic capacitance detection circuit further includes an inverting amplification circuit that inverts a signal at the signal output terminal, and
    an adding circuit that adds up an output signal of the voltage follower and an output signal of the inverting amplification circuit.

6. The electrostatic capacitance detection circuit according to claim 1,
    wherein the one end of the capacitor and the input terminal of the voltage follower are connected to each other by a non-shielded electric conductor.

7. The electrostatic capacitance detection circuit according to claim 1,
    wherein the capacitor and the electrostatic capacitance detection circuit are stored in a shield box.

8. An electrostatic capacitance detection device comprising:
    a capacitive sensor as the capacitor to be detected that detects a physical quantity according to a change in capacitance; and
    the electrostatic capacitance detecting circuit according to claim 1, which is implemented on a printed circuit board or a silicon substrate and fixed to the capacitive sensor.

9. A microphone device comprising:
    a capacitor microphone as the capacitor to be detected; and
        an electrostatic capacitance detection circuit according to claim 1.

* * * * *